United States Patent [19]

Brigham-Burke et al.

[11] Patent Number: 5,561,069

[45] Date of Patent: Oct. 1, 1996

[54] SURFACE PLASMON RESONANCE DETECTOR HAVING COLLECTOR FOR ELUTED LIGATE

[75] Inventors: Michael Brigham-Burke, King of Prussia; Daniel J. O'Shannessy, Limerick, both of Pa.

[73] Assignee: SmithKline Beecham Corporation, Philadelphia, Pa.

[21] Appl. No.: 342,511

[22] Filed: Nov. 21, 1994

Related U.S. Application Data

[62] Division of Ser. No. 88,006, Jul. 6, 1993, Pat. No. 5,395,587.

[51] Int. Cl.$^6$ .................................................. G01N 33/543
[52] U.S. Cl. ........................ 436/518; 356/317; 356/318; 385/12; 385/129; 385/130; 422/55; 422/57; 422/63; 422/82.05; 422/82.11; 435/808; 436/164; 436/165; 436/524; 436/525; 436/527; 436/529; 436/532; 436/805
[58] Field of Search .......................... 210/656; 356/317, 356/318, 445; 385/12, 129, 130; 422/55, 57, 63, 82.05, 82.11; 435/808; 436/164, 165, 518, 524, 525, 527, 529, 531, 532, 805

[56] References Cited

U.S. PATENT DOCUMENTS 5,242,828  9/1993  Bergström et al. ..................... 435/291
5,395,587  3/1995  Brigham-Burke et al. .......... 422/82.11

OTHER PUBLICATIONS

Sigma Catalog (1989), p. 174.
Sjölander et al, "Integrated Fluid Handling System for Biomolecular Interaction Analysis", *Anal. Chemistry*, 1991, 63, pp. 2338–2345.
Cole–Parmer Instrument Company (1991/1992), p. 147.
Fägerstäm et al, "Biospecific Interaction Analysis Using Surface Plasmon Resonance Detection . . .", *J. of Chromatography*, 597, (1992), pp. 397–410.

Primary Examiner—James C. Housel
Assistant Examiner—Christopher L. Chin
Attorney, Agent, or Firm—Herbert H. Jervis; Edward T. Lentz; Stephen A. Venetianer

[57] ABSTRACT

An improved surface plasmon resonance detector, capable of recovering a desired eluted ligate, permits the isolation and characterization of novel ligates and ligands.

4 Claims, 2 Drawing Sheets

SURFACE PLASMON RESONANCE DETECTOR HAVING COLLECTOR FOR ELUTED LIGATE

This is a divisional of application Ser. No. 08/088,006, filed Jul. 6, 1993, which issued as U.S. Pat. No. 5,395,587 on Mar. 7, 1995.

FIELD OF THE INVENTION

This invention relates generally to surface plasmon resonance detectors and more particularly to an improved plasmon resonance instrument having a feature allowing for the collection and subsequent analysis of ligate solutions following interaction of the ligate with an immobilized ligand on the surface plasmon resonance sensor.

The invention has utility in the micro-scale isolation and characterization of novel binding activities of proteins and peptides, and particularly in the isolation of specific antibody activities and identification of biologically significant peptide sequences.

BACKGROUND OF THE INVENTION

Surface plasmon resonance (SPR) is an optical phenomenon which occurs as a result of total internal reflection of light at a metal film—liquid interface. Total internal reflection is observed in situations where light travels through a medium such as glass, and is reflected back through that medium from the interface with a different medium, for example a liquid buffer solution. In order for total internal reflection to occur, the angle of incidence of the light must be greater than a critical angle determined by the refractive indices of the optical media. Although the light is totally reflected, a component of the incident light momentum, termed the evanescent wave, penetrates a distance, on the order of one wavelength, into the medium, e.g. the buffer, on the opposite side of the interface.

If the incident light is monochromatic and polarized, and the interface between the media is coated with a thin film of gold or silver having a thickness which is a fraction of the wavelength of the incident light, the evanescent wave can interact with free oscillating electrons, or plasmons, in the metal film surface. The plasmons will absorb energy from the evanescent wave at a particular angle of incidence, which is dependent upon the refractive index of the liquid medium adjacent to the metal film, i.e. within a distance of about 300 nm. from the metal film. Thus, for a given refractive index in the liquid, the intensity of the reflected light varies according to the angle of incidence of the light, and there is a sharp drop in the intensity of the reflected light at a particular angle at which peak absorbance occurs. This angle can be termed the "resonance angle." Changes in the refractive index of the buffer solution will alter the resonance angle. By measuring the angle at which the peak occurs, it is possible to detect changes in the refractive index of the buffer solution.

Because proteins in the buffer solution alter its refractive index, it is possible to measure, and monitor continuously, the protein content in the buffer solution adjacent to the metal film by measuring the resonance angle. The interaction of macromolecules in the buffer solution with surface immobilized ligand, e.g., antibody binding to peptide or protein, causes a change in the refractive index. This change results in a correlative change in the resonance angle which is detected and quantitated.

Surface plasmon resonance technology is utilized in commercially available instruments, for example, the BIAcore® SPR detector manufactured by Pharmacia Biosensor AB (Uppsala, Sweden).

The BIAcore® apparatus uses surface plasmon resonance to measure the binding affinity and avidity of selected ligates, e.g., immunoglobulins or other proteins and peptides, with an immobilized ligand of interest, e.g. an antibody.

The methodology relies on immobilization of ligands onto the surface of a sensor chip consisting of a glass substrate having a gold film covered by a monolayer of a long hydroxyalkyl thiol to which is covalently attached a thin layer of carboxymethylated dextran. The immobilization procedure is performed with the sensor chip in place in the instrument and is continuously monitored by the SPR detector. In this procedure, the carboxyl groups of the carboxymethyl dextran are activated by injection of a mixture of N-ethyl-N'-(dimethylaminopropyl) carbodiimide hydrochloride (EDC) and N-hydroxysuccinimide (NHS), both prepared in water. In a second step, the ligand (protein) is injected over the surface in a low ionic strength solution at a pH below the isoelectric point of the protein. Since only a fraction of the carboxyl groups are activated by the EDC/NHS mixture, the positively charged protein concentrates onto the surface of the sensor chip via electrostatic attraction, and simultaneously, the amines of the protein react with the NHS-esters resulting in the formation of amide-links between the protein and the dextran surface [S.L öfås et al, *J. Chem. Soc. Chem. Commun.*, 1526–1528 (1990)].

Residual NHS-esters remaining after ligand immobilization are then reacted with a solution of ethanolamine. Finally, the surface is subjected to an acid wash to remove nonocovalently adsorbed protein. The entire immobilization procedure, which typically takes less than 30 minutes, can be controlled by parameters such as protein concentration, protein solution ionic strength and pH, reagent (EDC/NHS) concentration and reaction times.

The sensor chip is contacted by a microfluidic cartridge which has formed on it a number of channels (typically four) which define the flow of samples across the surface of the sensor chip. The microfluidic cartridge, which is in place when the ligand is introduced to the sensor, contains pneumatic valves which control the flow of samples through the channels.

An unknown sample or ligate solution is introduced into the apparatus to contact the immobilized ligand. The interaction between ligand and ligate is observed directly by surface plasmon resonance techniques and the measurements recorded on a computer via a program such as Bialogue [Pharmacia].

In the conventional surface plasmon resonance instrument, the ligate is discarded to waste after interacting with the ligand.

SUMMARY OF THE INVENTION

The general object of this invention is to provide a method and apparatus whereby, following observation of the interaction of a ligate solution with an immobilized ligand by means of an SPR detector, an eluted ligate solution can be recovered for subsequent analysis.

Another object is to provide a simple modification to an existing SPR detector for recovering eluted ligate, which does not adversely affect the performance of the detector.

Briefly, in accordance with the invention, a surface plasmon resonance detector comprising a surface plasmon resonance sensor chip, optical means for directing light toward said sensor chip and for monitoring the resonance angle by detecting light reflected from said sensor chip, and means for conducting a ligate solution to and from said sensor chip, is improved by the provision of a receptacle for eluted ligate, and means, connected to said conducting means, for conducting eluted ligate to said receptacle, whereby eluted ligate can be recovered for subsequent analysis.

The invention provides for selectively recovering any binding activity, defined below, from a sample placed into contact with an immobilized ligand in an SPR detector. This permits a potentially novel molecule to be isolated and analyzed by conventional techniques. For example, a protein or peptide may be conventionally sequenced and subsequently cloned. The novel binding protein may be, for example, an antibody generated by standard hybridoma technology or by combinatorial approaches.

In another aspect, this invention provides a method for isolating novel binding activities, e.g., protein ligates, by using specific immobilized ligands in the detector, introducing a sample containing unknown ligates into the detector, determining the binding properties of the interacting ligand and ligate, and selectively collecting the eluted ligate which was measured using the modified SPR detector.

Other objects, details and advantages of the invention will be apparent from the following detailed description when read in conjunction with the drawings.

DETAILED DESCRIPTION

Figure 1:
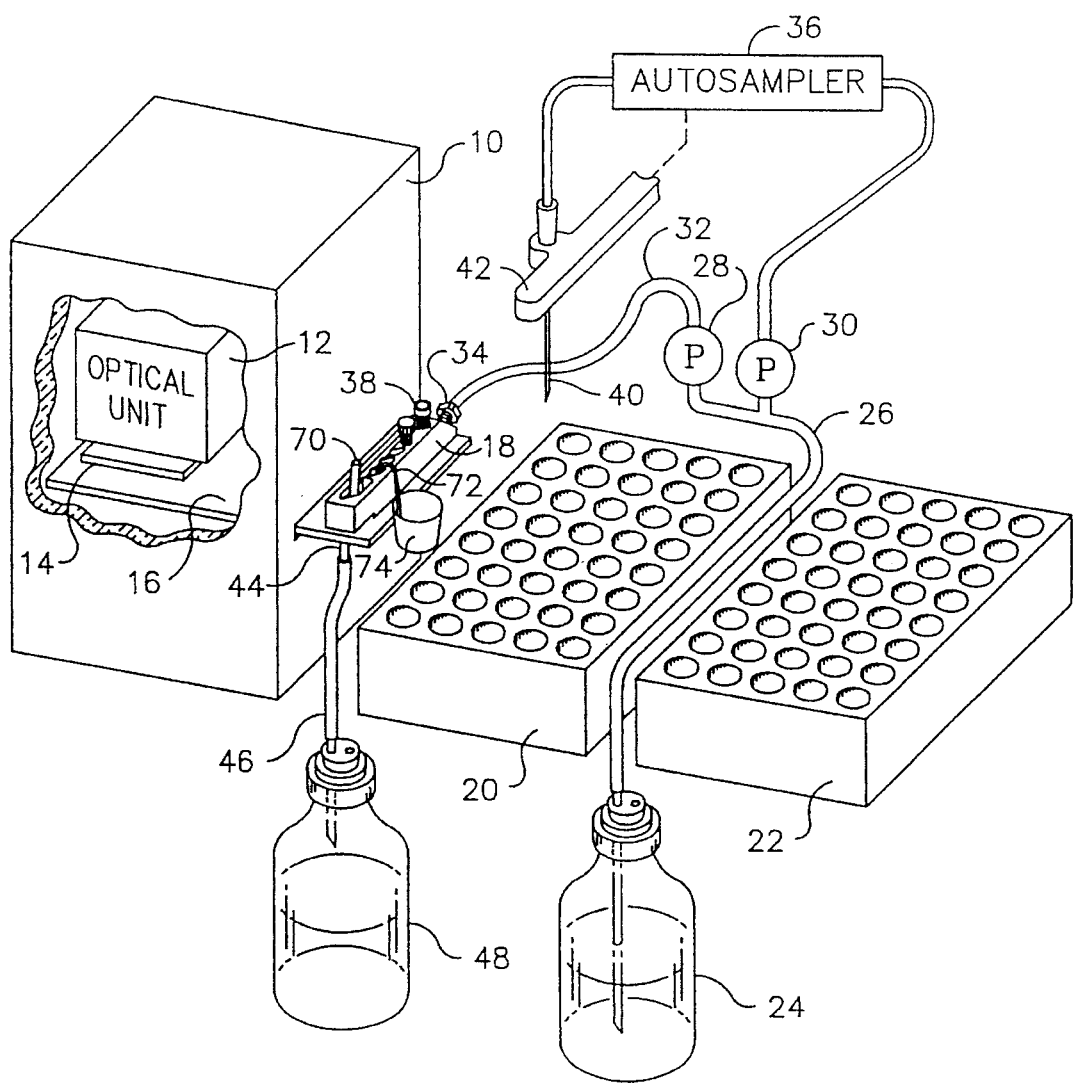
FIG. 1 is a schematic perspective view of a surface plasmon resonance instrument modified in accordance with the invention.

At the heart of the surface plasmon resonance detector is a sensor chip, at the surface of which plasmon resonance takes place. For details on the structure, composition and operation of the sensor chip, reference should be made to published international patent applications PCT/SE89/00642 and PCT/SE89/00643, both published May 17, 1990 and both of which are incorporated by reference herein.

As used herein, by the term "binding activity" is meant any protein or non-proteinaceous molecule or portion thereof which is capable of binding to an immobilized ligand, including without limitation, an antigen, antibody, protein, soluble receptor, DNA, RNA and phage libraries.

By the term "ligate" as used herein is meant any soluble binding activity.

By the term "ligand" as used herein is meant an immobilized protein or non-protein molecule.

Briefly, the sensor chip consists of a glass substrate onto which a thin gold film (50 nanometers in thickness), is deposited. The gold film is derivatized with a monolayer of a long hydroxyalkyl thiol. This monolayer serves two functions, as a barrier preventing proteins and other ligands from coming into direct contact with the metal surface, and as a functionalized layer for further derivitization. Covalently attached onto the hydroxyalkyl thiol is a 100 nm layer of carboxymethyl dextran. This dextran layer serves as a hydrophilic layer suitable for macromolecular interaction studies, and for containing functional groups available for ligand immobilization chemistries.

However, the inventors have determined that additional functional groups can be incorporated into the dextran layer. The present invention thus provides several alternative chemistries for immobilization of ligands onto the sensor chip surface, such as the amine, hydrazide and maleimide derivatives described in Examples 2 through 4 below. [See, also, D. O'Shannessy et at, *Analytical Biochem.*, 205:132–136 (August, 1992) incorporated by reference herein].

In each case, the carboxymethylated dextran surface was activated with a mixture of EDC and NHS as described above. Subsequent derivatization was performed to generate amine-derivatized, hydrazino-derivatized, sulfhydryl-derivatized or maleimide-derivatized surfaces allowing for the immobilization of a variety of functionalized ligands. In addition, the introduction of these chemistries allow for the site-directed immobilization of ligands, in particular antibodies, onto the sensor chip surface which has been demonstrated to be of value in chromatographic systems with respect to molar binding capacities. Indeed, the carboxymethylated dextran surface of the sensor chip can be considered as a micro-chromatographic matrix and numerous chemical approaches to the immobilization of ligands should be possible, assuming the reagents used are compatible with the hardware of the instrument.

It is contemplated by the present inventors that yet other chemical modifications may be made to the immobilizing procedure described herein. For example some other polymer may be used to change the chemistry of the surface chips. Chromatographic polymers, methacrylate polymers, and other inert materials exhibiting low non-specific binding properties may also be used to modify the surface chips.

The modified SPR device operates as follows. Plane polarized light from a high efficiency, near-infrared light emitting diode is focused into a transverse wedge through the prism, and onto the side of the sensor chip opposite the gold-film. Reflected light is monitored by a fixed, two-dimensional array of light sensitive diodes positioned to achieve a resolution of approximately 0.1° in the angle of reflection. Computer interpolation routines process the data from the diode array to determine the resonance angle to an accuracy of $10^{-4}$°. Averaged readings are ordinarily obtained at a frequency of 5 Hz, but may be varied if desired. The use of a fixed diode array detector eliminates moving parts from the optical system, allowing changes in the resonance angle to be detected in real time.

By continuously monitoring the refractive index, detected as a change in the resonance angle, and plotting this value as a function of time, a sensorgram is obtained. For the average protein, a 0.1° shift in the surface plasmon resonance angle is equivalent to a surface concentration change of 1 ng/mm$^2$. The total range covered by the SPR detector is 3°. The resonance signal at any given point in time is the sum of contributions from the sensor chip surface, interacting molecules and the bulk solution. When the bulk solution refractive index is constant, the amount of interacting molecule can be monitored continuously. If, on the other hand, the refractive index of the ligate solution differs from that of the continuous buffer flow, the amount of interacting ligate may be quantitatively measured from readings taken between sample injections where refractive index buffer flow is constant. For kinetic measurements where the progress of the binding curve rather than the absolute response value are used, correction for sample bulk refractive index is not necessary.

The methodology relies on immobilization of ligands onto the carboxymethylated dextran or other functional group present on the sensor chip, as discussed in the background. Essentially, the improvement of this invention permits any immobilization procedure to be adapted to operate in the modified instrument to enable the identification of a variety of proteinaceous or non-proteinaceous binding activities. The binding activities determined by the use of this improved instrument are essentially independent of the immobilization procedure. For example, it should be noted that protein (ligand) concentrations used for immobilization are usually only in the range of 20–30 μg/ml and since only 100 μ is required, a total of only 2–3 μg of ligand is needed. Reproducibility studies for the immobilization of three different proteins onto 150 sensor chips shows a precision of better than 4% relative standard deviation. This value includes errors in the preparation of reagents, variability in the sensor chips per se, as well as instrument performance. Depending on the stability of the immobilized ligand, the sensor surface can be regenerated and used for a number of analytical determinations.

The surface plasmon resonance detection instrument, as shown in FIG. 1, comprises a thermally insulated housing 10 having, in its interior, an optical unit 12, a sensor chip 14 and a microfluidic cartridge 16, the latter extending outward through a slot in the housing and having its external portion coupled to a connector block 18. A pair of temperature-controlled racks 20 and 22 is provided for holding sample vials. A buffer solution bottle 24 is connected through tube 26 to a pair of pumps 28 and 30.

Pump 28 is connected to block 18 through tube 32. The purpose of pump 28 is to maintain a constant flow of liquid over the surface of the sensor chip. Buffer solution flows through an inlet port 34 in block 18, and through an internal passage in the block, to a channel in the microfluidic cartridge through which it is carried to sensor chip 14.

Pump 30 is used in conjunction with an autosampler, schematically indicated at 36, to transfer samples from vials in the vial racks to an injection port 38 in the connector block. Transfer of samples is carried out by means of a needle 40 carried on a delivery arm 42, which is pan of the autosampler.

The connector block has a drain port 44, which is connected through a tube 46 to a waste collection bottle 48.

A computer (not shown) controls the operation of the autosampler to transfer samples from the vials to the injection port of the connector block in a predetermined sequence. The computer controls the operation of the microfluidic cartridge, so that sample plugs are sequentially delivered into the buffer stream passing continuously across the surface of the SPR sensor chip. The computer also performs data acquisition and analysis.

Figure 2:
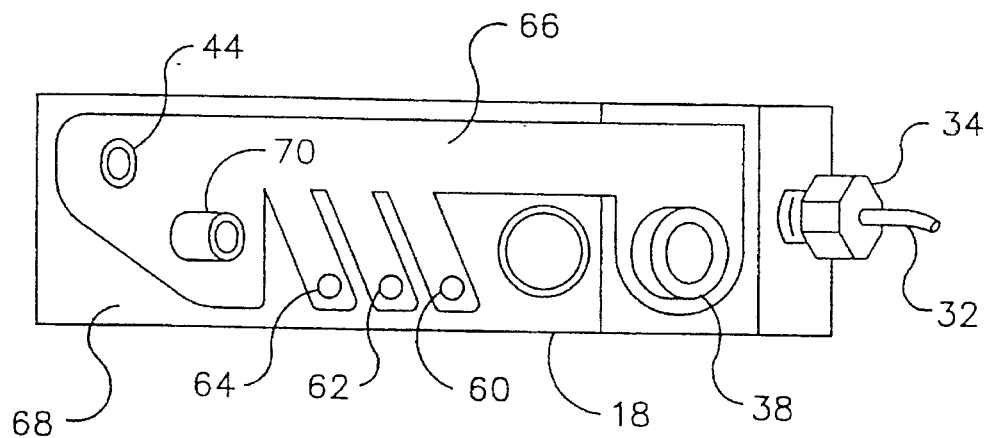
FIG. 2 is a top plan view of a connector block of the instrument.
Figure 3:
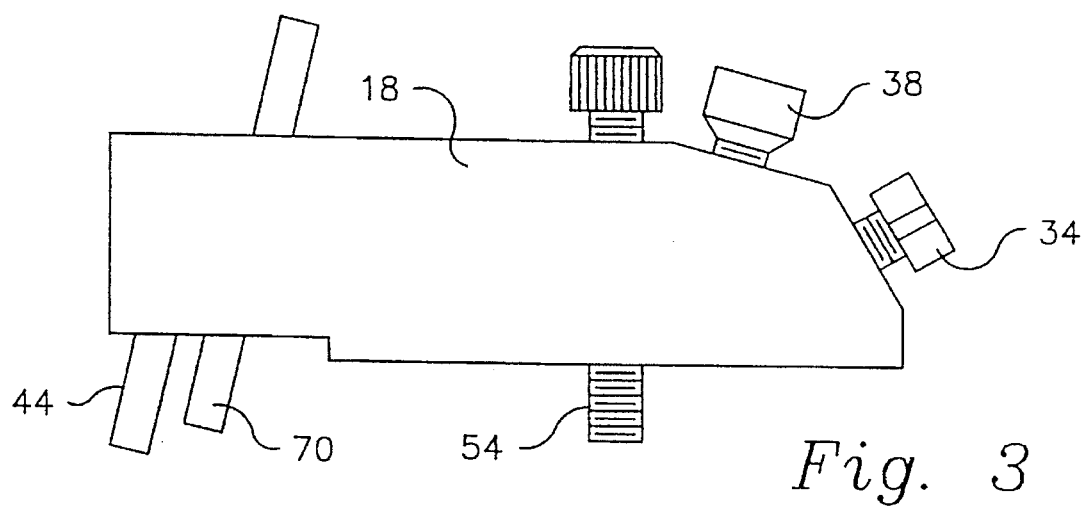
FIG. 3 is a side elevation of the connector block.
Figure 4:
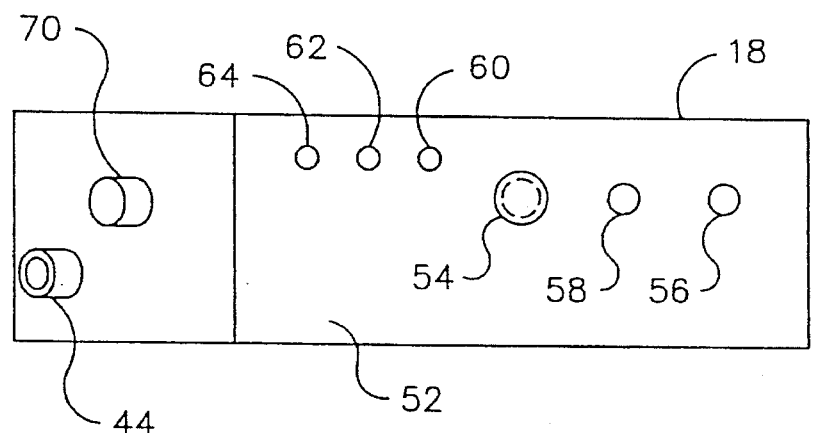
FIG. 4 is a bottom plan view of the connector block.

Referring to FIGS. 2–4, the connector block is a molded synthetic resin block having internal passages for making connections to passages in the microfluidic cartridge. FIG. 4 demonstrates only one configuration of a connector block which can perform the functions described herein. However, it should be understood by one of skill in the art that other configurations adapted for the reuse of the binding activity may be readily designed, which are encompassed by this invention.

The microfluidics cartridge [Sjolander and Urbaniczky, *Anal. Chem.*, 63:2338–2345 (1991)] contains two identical sets of pneumatic valves and channels, each with two sample loops for injection volumes of between 5 μL to 45 μL. Located at the surface of the cartridge is a flow cell with four channels. When the cartridge is docked with the sensor chip, four parallel flow cells each with a volume of 60 nL are formed. The four flow cells, which are illuminated simultaneously by the transverse wedge of light, can be connected to any of the sample loops through the pneumatic valves.

The bottom face 52 of the connector block has a set of openings which mate with openings in the upper surface of the microfluidic cartridge when the connector block is secured to the cartridge by means of a locking screw 54. The openings include an opening 56, which is connected to buffer inlet port 34, an opening 58, which is connected to injection port 38, and openings 60, 62 and 64, which are connected to an open common channel 66 formed in the upper surface 68 of the block, as shown in FIG. 2. Openings 60, 62 and 64 carry waste from the microfluidic cartridge into common channel 66, which delivers it to drain port 44. Opening 60 carries waste produced when the injection port is washed with buffer. Opening 62 carries waste from the flow through fluidic channel loops in the microfluidic cartridge. Opening 64 carries waste which from the four channels which define the flow of samples across the surface of the sensor chip. Tube 70, which extends through the connector block, has a closed bottom, and is provided for washing needle 40.

In the ordinary operation of the surface plasmon resonance instrument, samples of soluble binding activity are injected into injection port 38 on the connector block, and delivered through opening 58, from which they are carried through channels in the microfluidic cartridge. The samples join streams of continuously flowing buffer solution, under the control of air-operated microfluidic valves, and are delivered to the channels extending across the surface of the sensor chip. If the unknown ligate is capable of binding to the immobilized ligand, the ligate in the samples will bind the ligand, and excess unbound ligate will continue in the buffer flow.

The streams from these channels join one another to form a single stream, which flows to opening 64. Opening 64 connects this single stream to common channel 66, which carries it, along with other waste liquid, to drain port 44, through which the waste liquid is delivered to bottle 48.

Returning now to FIG. 1, one end of a narrow, flexible, capillary tube 72 fits snugly into the upper end of opening, 64 and is arranged to deliver waste (eluted ligate) from opening 64 to a collection receptacle 74. This receptacle can be a simple glass vial, test robe or similar vessel, or a glass or polymeric filter, such as nitrocellulose or PDF or any other suitable receptacle. The type of receptacle will depend on the intended additional technologies to be performed on the eluted binding activity. For example, if the binding activity is a protein, the receptacle can be a nitrocellulose filter for direct introduction into a protein sequencer.

Alternatively, the receptacle function may be performed by the tubing itself which is configured to transfer the eluted binding activity directly into another instrument, such as a sequencer or a mass spectrometer.

Preferably, however, the capillary tube typically has an internal diameter of 0.06 mm and should be as short as possible in length in order to minimize "dead volume", i.e. the volume of liquid remaining in the tube after a desired volume of liquid is collected in the receptacle.

The improved SPR instrument of this invention provides a method for isolating novel soluble binding activities (ligates) by using specific immobilized ligands in the detector, putting a sample containing unknowns into the detector, visually identifying the interacting ligates, and selectively collecting the eluted ligates which were observed using the modified SPR detector.

Once collected, the ligates may be isolated using conventional techniques and subjected to further analysis, for example, sequencing, amplification and other techniques the selection of which depends on the nature of the binding activity collected by this method. From such analysis of a protein binding activity, specific oligonucleotide probes may be designed and the protein cloned using conventional techniques [Sambrook et al, *Molecular Cloning. A Laboratory Manual*, 2d edition, Cold Spring Harbor, New York (1989)]. In addition, amino acid sequence information derived from protein ligates may be used to generate specific antibodies against the protein ligate. Such antibodies may be generated using conventional techniques.

Further, this invention provides a method for isolating and characterizing specific novel binding activities, for example, as displayed on phage libraries. This method involves introducing into the SPR device as the ligate all or portions of the phage libraries and contacting the immobilized peptide ligands therein. Identification of the ligates which interact with the immobilized peptides permits antibodies, or peptide fragments having antibody-like activity in the phage libraries, to be further characterized.

The isolation of the specific phage library binding activity via, e.g., passage through bacteria and reselection, is crucial for the identification and subsequent use of the binding activities in the development of pharmaceuticals.

The following examples describe several aspects of the operation of the improved device according to this invention, including alternative immobilization chemistries. These examples are provided for illustration only and do not limit the scope of this invention.

The materials employed in the examples included the BIAcore instrument, sensor chips CM5, surfactant P20, and the amine coupling kit containing NHS, EDC, and ethanolamine [Pharmacia Biosensor of Uppsala, Sweden]; sulfosuccinimidyl-6-(biotinamido)hexanoate (NHS-LC-biotin), sulfosuccinimidyl-2- (biotinamido)ethyl-1,3-dithiopropionate (NHS-SS-biotin), and biotin-LC-hydrazide [Pierce Chemical Co., Rockford, ILL.]; affinity-purified avidin and streptavidin, m- maleimidobenzoyl-N-hydroxysulfosuccinimide ester (sulfo-MDS) and 2-iminothiolane (Traut's reagent) [Pierce Chemical Co.]; human immunoglobulin G (IgG) [Calbiochem Corp., San Diego, CA.]; hydrazine hydrate and bovine serum albumin (BSA) [Sigma Chemical Co., St. Louis, MO.]and ethylenediamine [Aldrich Chemical Co., Milwaukee, WI.]. All other reagents were of analytical grade.

Example 1

Purification of a Protein Antigen using Immobilized Monoclonal Antibody

A. Immobilization of L-71

The commercially available anti-sCD4 monoclonal antibody L-71 was immobilized onto the sensor surface via NHS/EDC coupling using a solution of 100 µg/ml of MoAb in 10 mM NaOAc pH 4.7. Using the standard immobilization routine, 14,000 Response units (Ru) of L-71 were coupled to the surface. The layer was washed 5 times with 0.1 M $H_3PO_4$ to remove any noncovalently coupled L-71 that may contaminate eluted sample later. Using a 1 mg/ml solution of sCD4 the Rmax of the surface was determined to be 5100 Ru or 0.1 pmole of sCD4.

B. Determination of Dead Volume from Sensor Surface to the Collection Tube

In order to predict when the eluted sample will emerge from the modified outlet the following experiment was performed. The buffer flow of the BIAcore was set to 25 µlmin. A 50 µsample of 0.01% pyroniny dye (commercially available) was injected. After the sample was loaded and injected fractions were collected every minute. The dye passed through the sensor cell and into the fraction tube in approximately three minutes. Therefore the dead volume is approximately 75 µgl.

C. Collection of Eluted sCD4 from the L-7 Modified Layer

A method for the BIAcore was designed such that sCD4 would be repeatedly loaded and eluted from the sensor surface. The eluate could be collected by hand, or preferably, using a fraction collector. In this case a fraction collector was used to collect 100 µfractions from the BIAcore. The BIAcore flow- rate was set at 20 µgl/min. 50 gl of sCD4 were injected each time and eluted with 0.1 M $H_3PO_4$. The method was written to make 50 injections providing 5 pmoles of protein. The eluted fraction was then loaded onto a PVDF membrane for sequencing.

D. Determination Of Molecular Weight of a Protein Isolated from BIAcore Surface

Protein was collected from the sensor surface as before, except eluting with 0.1 M HCl, a volatile buffer. The sample is lyophilized in a Speed Vac. The dried protein is then reconstituted in a minimum amount of SDS-PAGE sample buffer and loaded onto a gel. The gel is developed and then proteins are transblotted onto PVDF. The protein is visualized by biotinylation followed by incubation with Strepavidin conjugated with horseradish peroxidase, followed by chemiluminescent detection.

E. Interfacing with Capillary Liquid Chromatography

This example is similar to the use of the fraction collector except that the outlet robing interfaces with or is pan of a capillary chromatograph. A sample of crude protein is injected onto the sensor surface of the BIAcore. The unbound fraction of the sample passes through and is not collected. The ligate is then eluted from the sensor surface and is collected onto the head of a capillary column. This procedure is repeated as needed. Instead of the eluted ligate binding to a membrane, it concentrates at the head of the capillary. It can then be eluted using a gradient elution method into a mass spectrometer or sequencer.

Example 2

Immobilization Chemistry - Immobilization of Proteins via Primary Amines

Immobilization of proteins (avidin, streptavidin) onto the NHS-ester-activated sensing surface was performed according to the manufacturers specifications using an automated program. Briefly, after equilibration of the sensing surface with Hepes buffer (HBS; 10 mM Hepes, 150 mM NaCl, 0.05% surfactant P20, pH 7.4), the following sample injections were made using the automated robotics unit incorporated into the BIAcore instrument: (i) equal volumes of NHS (0. 1 M in water) and EDC (0. 1 M in water) were mixed after which 30 µl was injected across the surface to activate the carboxymethylated dextran; (ii) 30 µl of 40 µl/ml solution of the ligand (protein) prepared in 10 mM sodium acetate buffer, pH 4.7, was then injected across the activated surface; (iii) residual NHS-esters were deactivated by a 30-μl injection of 1 M ethanolamine, pH 8.5; (iv) noncovalently bound ligand was washed from the surface by injecting 15 μl of 0.1 M phosphoric acid. The immobilization protocol is performed with a continuous flow of HBS of 5 μl/min.

To convert the sensing surface to the amine derivative, the carboxymethylated dextran was first "activated" with EDC/NHS as described above. To demonstrate that this reaction had indeed occurred, the amine-derivatized surface was subsequently reacted with NHS-activated surface as follows. The NHS-esters were reacted with ethylenediamine: 30 μl of a 1 M solution in water, pH 8.5, to generate the amine.

The amine-derivatized surface was subsequently reacted with NHS- LC-biotin and probed with streptavidin as follows. The amine-derivatized surface was biotinylated by injecting 30 μl of a 50 mM solution of NHS-LC-biotin prepared in 25 mM sodium bicarbonate, pH 8.5, at 5 μl/min. After washing the layer with 0.1 M phosphoric acid, streptavidin (30 μl, 50 μl/ml HBS) was then injected. The immobilized streptavidin layer was finally washed with 3 ×30 μl of 0.1 M phosphoric acid. As expected due to the high affinity constant for the streptavidin-biotin interaction, 0.1 M phosphoric acid did not disrupt this complex.

In a further demonstration of the specificity of the above-described experiments, NHS-SS-biotin was used in place of the NHS-LC-biotin. NHS-SS-biotin contains a disulfide which should be susceptible to reduction by such agents as dithiothreitol (DTT). After binding of streptavidin, the biotin/streptavidin complex was cleaved from the surface by injecting 2 ×30μl of 1 M DTT (in water). The results of this experiment show that the layer was biotinylated, as judged by streptavidin binding, and that the surface could be "regenerated" by injecting 1 M DTT, cleaving the biotin-streptavidin complex from the surface. A cleavable linkage such as a disulfide may be useful for the sequential immobilization/regeneration of the same activated surface with a number of ligands.

Taken together therefore, these experiments demonstrate that the sensing surface of the BIAcore can be readily derivatized to a primary amine and that further derivatization of the amine, e.g., with biotin, is possible. The amine-derivatized surface can therefore be used as an intermediate in the preparation of other functionally active surfaces, as described below. In addition, disulfides can be efficiently cleaved using DTT or β-mercaptoethanol. The results clearly demonstrate that the layer did biotinylate since streptavidin was able to bind to the derivatized surface. The amount of streptavidin immobilized onto the biotinylated surface was approximately sevenfold higher than that seen on immobilization of streptavidin directly onto the NHS-ester-activated surface.

It should also be noted that prior derivatization of the surface with ethylenediamine was essential for the reaction with NHS-LC-biotin. When the NHS-LC-biotin was replaced with a 30-μl injection of ethanolamine or HBS, no streptavidin bound to the surface demonstrating that the streptavidin was indeed binding to the immobilized biotin.

The data on the immobilization of avidin and streptavidin via primary amines demonstrated that avidin was more readily immobilized onto the sensing surface than streptavidin, although streptavidin was able to diffuse into the dextran layer. The relatively poor immobilization of streptavidin under conditions identical to those used for immobilization of avidin, most likely results from the number of available lysines on the two molecules (avidin contains 36 lysines per tetramer; streptavidin contains 12 lysines per lettamer).

This experiment serves to demonstrate one of the disadvantages of the NHS-ester immobilization chemistry, i.e., the difficulty in immobilizing proteins with limited lysines. In addition, the amount of streptavidin immobilized directly onto the sensing surface acts as a "baseline" for the experiments to be detailed below. Both the immobilized avidin and streptavidin surfaces could be used to "immobilize" biotinylated proteins, such as human IgG.

Example 3

Hydrazide Derivatization of the Sensing Surface.

The hydrazide derivative of the sensing surface was prepared as described for the amine derivative of Example 2 except that 1 M hydrazine, pH 8.5, was used. The NHS-ester-activated sensing surface was activated with biotin-LC-hydrazide (20 mM in 10 mM sodium acetate, pH 4.7; 30 μl injection) followed by 30 μl of 1 M ethanolamine. The layer was then washed with 0.1 M phosphoric acid.

As described above, the "biotifiylated" surface was probed with streptavidin (30 μl, 50 μg/ml HBS), which was allowed to associate with the layer after which 4 ×30 μl of 0.1 M phosphoric acid was injected. The results demonstrate that biotin-LC-hydrazide reacted with the sensing surface and that streptavidin was able to bind to the immobilized biotin.

30 μof M hydrazine, pH 8.5, was injected across the EDC/NHS-activated surface. After injection of 30 μl of 1 M ethanolamine, the layer was washed with 15 μl of 0.1 M phosphoric acid. Oxidized human IgG (50 μl, 100 μg/ml sodium acetate, pH 5.5) was injected across the layer followed by 2 ×30-μl washes with 0.1M phosphoric acid and bound thereto.

Such a hydrazide derivatized sensing surface is useful for the site-directed immobilization of glycoconjugates, particularly antibodies [O Shannessy et at, Anal Biochem., 191:1–8 (1990)]. The hydrazide-derivatized surface can be used for the immobilization of oxidized IgG, specifically through the carbohydrate. It should be noted that unoxidized IgG did not immobilize onto the hydrazide surface.

Example 4

Immobilizations of SH-Containing Proteins onto a Maleimido-Derivatized Sensing Surface.

To prepare a maleimido-derivatized surface, the surface was first convened to the amine, as described in Example 2. Fifty microliters of a 50 mM solution of the heterobifunctional reagent sulfo-MBS prepared in 25 mM sodium bicarbonate, pH 8.5, was then injected. To demonstrate sulfhydryl reactivity, the surface modification was probed by injecting 50 μof Traut's modified BSA (100 μg/ml of 25 mM sodium bicarbonate, pH 8.5). BSA was immobilized.

Replacing unmodified BSA for the Traut's modified BSA resulted in no binding demonstrating the specificity of the reactions. This approach may be used for the site-specific immobilization of peptides containing cysteine at either the carboxy- or amino-terminus.

By chemical derivatization of the sensing surface of the BIAcore surface plasmon resonance detector, the user may choose an immobilization strategy most suited for the ligand and interaction under study. The ability to site-direct the immobilization chemistry to particular groups on the ligand, as with hydrazide or sulfhydryl chemistries, has been shown to be advantageous in the chromatographic mode.

Numerous modifications and alterations can be made to the apparatus and processes of the invention without departing from its scope as defined in the following claims.

What is claimed is:

1. A surface plasmon resonance detector comprising:

a sensor chip having a modified dextran derivative on the surface of said sensor chip for immobilizing ligands other than those containing primary amino groups;

means providing an inlet for receiving a ligate solution to be conducted to said sensor chip;

means providing an outlet port allowing for discharge of eluted ligate conducted from said sensor chip;

a receptacle for collecting said eluted ligate;

an external conduit having a first end removably connected to said outlet port and a second end received by said receptacle;

whereby when said external conduit is connected to said outlet port, said eluted ligate can be recovered in said receptacle for subsequent analysis, and further comprising a connector block integrally connected to said means providing an inlet port and said means providing an outlet port, said connector block having an open channel and a drain port in communication with said open channel, whereby when said external conduit is disconnected from said outlet port, said eluted ligate is discharged out of said outlet port, into said open channel and through said drain port as waste.

2. A surface plasmon resonance detector according to claim 1, wherein said means providing an outlet port projects from said connector block, and wherein a portion of said external conduit is capable of fitting snugly over said means providing an outlet port to provide a seal between said external conduit and said outlet port, whereby said eluted ligate is directed to said receptacle.

3. A method of isolating a molecule characterized by a desired binding activity comprising the steps of:

(a) immobilizing a known ligand on a sensor chip in a surface plasmon resonance detector comprising a surface plasmon resonance sensor chip, optical means for directing light toward said sensor chip and for monitoring the resonance angle by detecting light reflected from said sensor chip, and means for conducting a ligate solution containing said molecule to and from said sensor chip, wherein said means for conducting is a microfluidic cartridge in contact with said sensor chip and a connector block having means for transferring eluted ligate to a selected instrument, coupled to said microfluidic cartridge;

wherein said connector block comprises an injection port, an open channel, a drain port in communication with said open channel, and a drain passage leading from said microfluidic cartridge and having an end opening into said open channel; and wherein said transferring means to said instrument fits into said end opening and leads to said instrument; whereby eluted ligate can be subsequently analyzed;

(b) injecting a ligate solution sample comprising said molecule into said detector;

(c) observing the detector for any interaction between ligand and said molecule;

(d) collecting the molecule as it is eluted from said detector; and (e) isolating the eluted molecule.

4. A method of identifying a molecule characterized by a desired binding activity comprising the steps of:

(a) immobilizing a known ligand on a sensor chip in a surface plasmon resonance detector comprising a surface plasmon resonance sensor chip, optical means for directing light toward said sensor chip and for monitoring the resonance angle by detecting light reflected from said sensor chip, and means for conducting a ligate solution containing said molecule to and from said sensor chip, wherein said means for conducting is a microfluidic cartridge in contact with said sensor chip and a connector block having means for transferring eluted ligate to a selected instrument, coupled to said microfluidic cartridge;

wherein said connector block comprises an injection port, an open channel, a drain port in communication with said open channel, and a drain passage leading from said microfluidic cartridge and having an end opening into said open channel; and wherein said transferring means to said instrument fits into said end opening and leads to said instrument; whereby eluted ligate can be subsequently analyzed;

(b) injecting a ligate solution sample comprising said molecule into said detector;

(c) observing the detector for any interaction between ligand and said molecule;

(d) transferring the interacting molecule to a selected instrument; and (e) identifying said molecule by subjecting it to further analysis in said instrument.

* * * * *